United States Patent [19]
Garrett

[11] Patent Number: 4,773,230
[45] Date of Patent: Sep. 27, 1988

[54] SELF-CONTAINED REFRIGERATED MOBILE MORTUARY

[75] Inventor: Roger L. Garrett, Grosse Pointe Park, Mich.

[73] Assignee: Lipshaw Corporation, Detroit, Mich.

[21] Appl. No.: 45,388

[22] Filed: May 4, 1987

[51] Int. Cl.[4] .................................................. F25D 15/00
[52] U.S. Cl. .......................................... 62/237; 62/236; 62/244; 27/11; 27/28
[58] Field of Search .................... 62/244, 236, 237; 27/11, 28, 35

[56] References Cited
U.S. PATENT DOCUMENTS

| | | | |
|---|---|---|---|
| 2,612,761 | 10/1952 | Hilker | 27/28 |
| 3,034,843 | 5/1962 | Moon | 27/28 |
| 4,584,841 | 4/1986 | Guillaume et al. | 27/11 X |

Primary Examiner—Lloyd L. King
Attorney, Agent, or Firm—Barnes, Kisselle, Raisch, Choate, Whittemore & Hulbert

[57] ABSTRACT

A mobile mortuary comprising an elongated container defining an interior compartment for cadavers. Cadaver trays are supported in the compartment for movement through an opening in the front wall of the container to an extended position. An evaporator is mounted on the container within the compartment, and a compressor-condenser unit and generator are mounted on the container outside the compartment. The mortuary is mounted on wheels for movement upon a supporting surface.

8 Claims, 2 Drawing Sheets

U.S. Patent  Sep. 27, 1988  Sheet 2 of 2  4,773,230
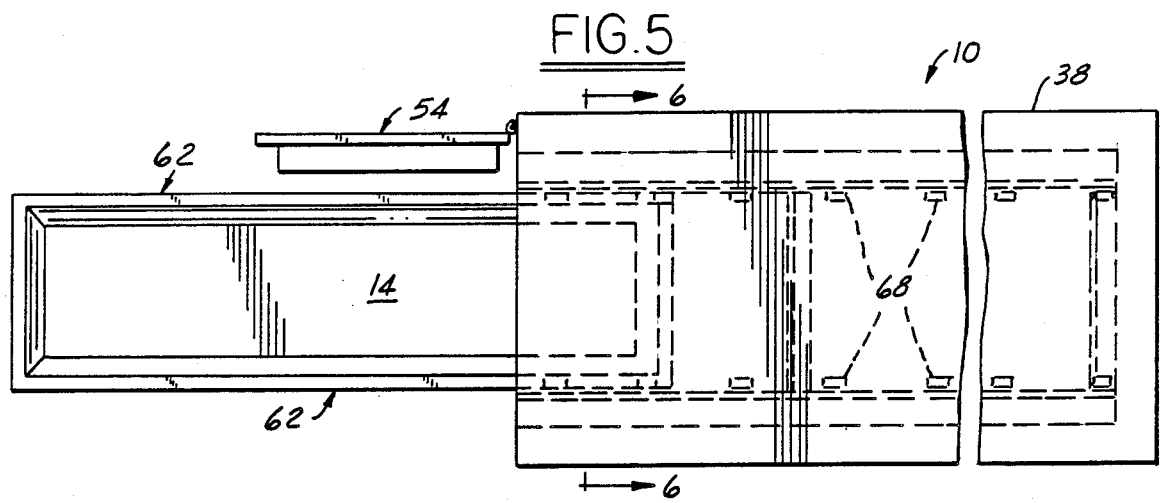
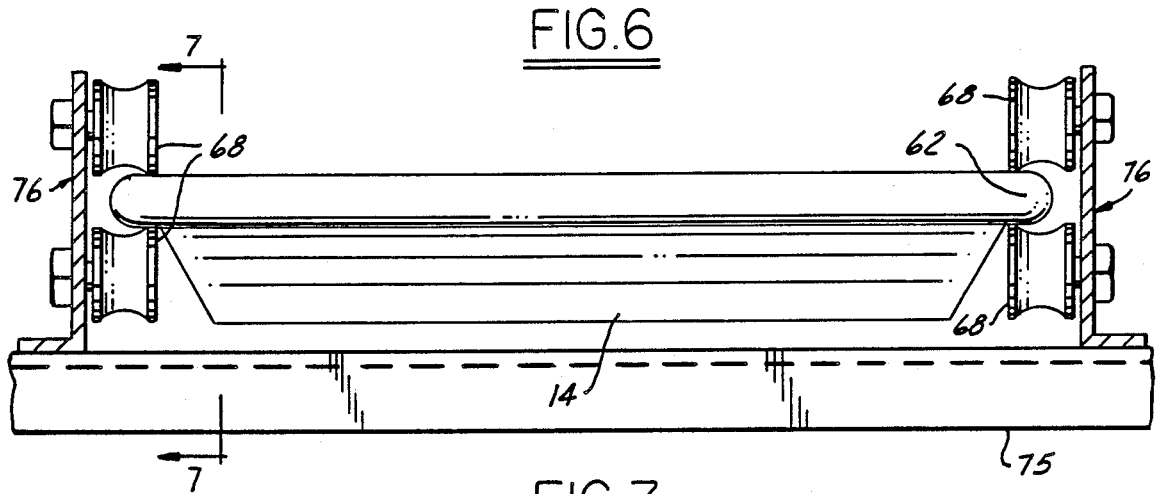
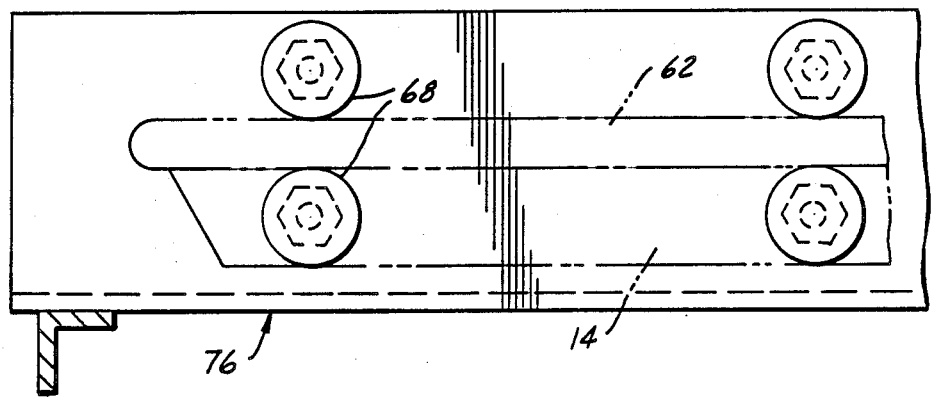

SELF-CONTAINED REFRIGERATED MOBILE MORTUARY

This invention relates generally to mortuaries and refers more particularly to a self-contained refrigerated mobile mortuary.

SUMMARY OF THE INVENTION

The mortuary of this invention is completely mobile and highly versatile. It is self-contained, having a built-in evaporator and condensing unit. The compressor-condensor unit is capable of converting easily to the available source of power, either AC or DC, any place in the world. The mortuary is also equipped with a generator so that it can be used where there is a lack of power.

The mobile mortuary provides temporary storage of cadavers during overcrowded or emergency conditions or in facilities where space for a permanently installed mortuary is not available, especially where the need for an economical, practical and effective system for preservation is imperative.

While the mobile mortuary of this invention has been designed in particular for use in third world countries and other places where power is not available, it has many uses and can fill a variety of needs in hospitals, medical schools, laboratories, and funeral homes. It would be invaluable in case of a major disaster or military conflict.

These and other objectives and features of the invention will become more apparent as the following description proceeds, especially when considered with the accompanying drawings.

BRIEF DESCRIPTION OF THE DRAWINGS

FIG. 5 is a top plan view showing a cadaver tray extended.

FIG. 6 is a sectional view taken on the line 6—6 in FIG. 5.

FIG. 7. is a fragmentary sectional view taken on the line 7—7 in FIG. 6.

DETAILED DESCRIPTION

Figure 1:
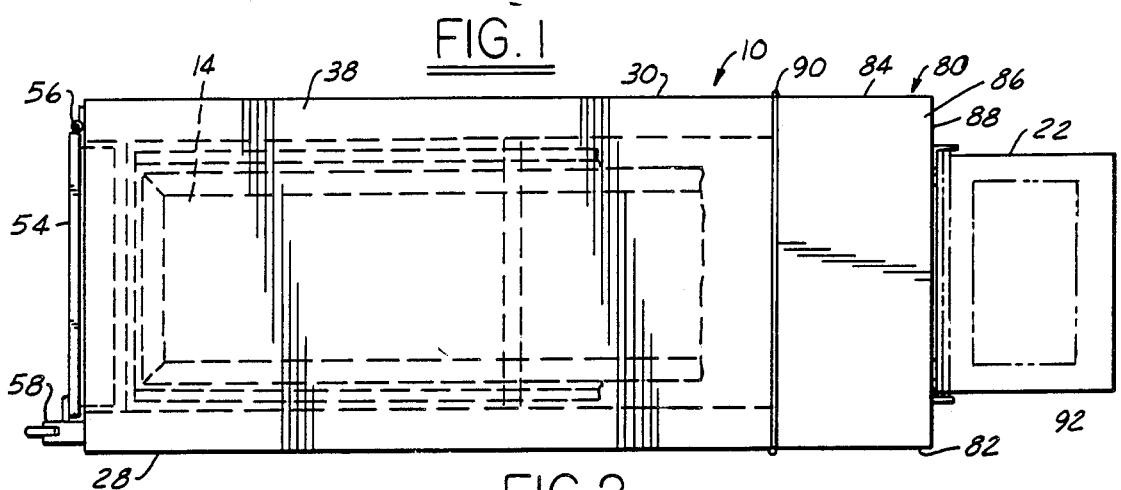
FIG. 1 is a top plan view of a self-contained, refrigerated mobile mortuary constructed in accordance with the invention.

Referring now more particularly to the drawings, the self-contained mortuary there shown comprises a container 10 providing an interior space or compartment 12 for cadaver trays 14 and 16, an evaporator 18, a compressor-condensor unit 20, a generator 22, and wheels 24 for supporting the mortuary for movement on a supporting surface.

The container 10 is an elongated box like structure having a horizontal, rectangular bottom wall panel 26 and parallel side panels 28 and 30 extending vertically upwardly from opposite side edges of the bottom panel. The side panels are rectangular, except at the upper rear corners where they are notched to form cut-away portions defined by vertical and horizontal edges 32 and 34.

The top wall of the container has a horizontal, rectangular panel 38. The rear wall is a vertical, rectangular panel 42. The top and rear walls at the rear and top edges of panels 38 and 42 have vertical and horizontal portions 44 and 46, respectively, which extend along the vertical and horizontal edges 32 and 34 of the side panels and together define an exterior recess 48.

The front wall is a panel 50 which is vertical and parallel to the rear panel. The front panel has an opening 52 extending upwardly from the bottom panel 26. A door 54 is hinged at one side edge where indicated at 56 for swinging movement to open and close the opening 52. A suitable handle and latch structure 58 is provided at the swinging edge of the door.

The bottom panel 26, side panels 28 and 30, top panel 38 and rear panel 42, including the recess forming portions of the top and rear panels, are provided with suitable heat insulating material. The door 54 is similarly insulated.

Within the interior compartment 12 of the container 10 and extending lengthwise thereof, are two cadaver trays 14 and 16 supported one above the other for sliding movement. The outside edges of the trays have rolled edges 62 to ride on rollers 68. Rollers 68 are contoured to fit the rolled edges 62 of the trays. Rollers 68 are bolted to longitudinally extending fixed horizontal bars 76 above and below the rolled edges 62 of the trays so as to hold the trays in horizontal position when extended through opening 52. Bars 76 are mounted on cross bars 75 which are connected to front and rear panels 50 and 42.

Figure 2:
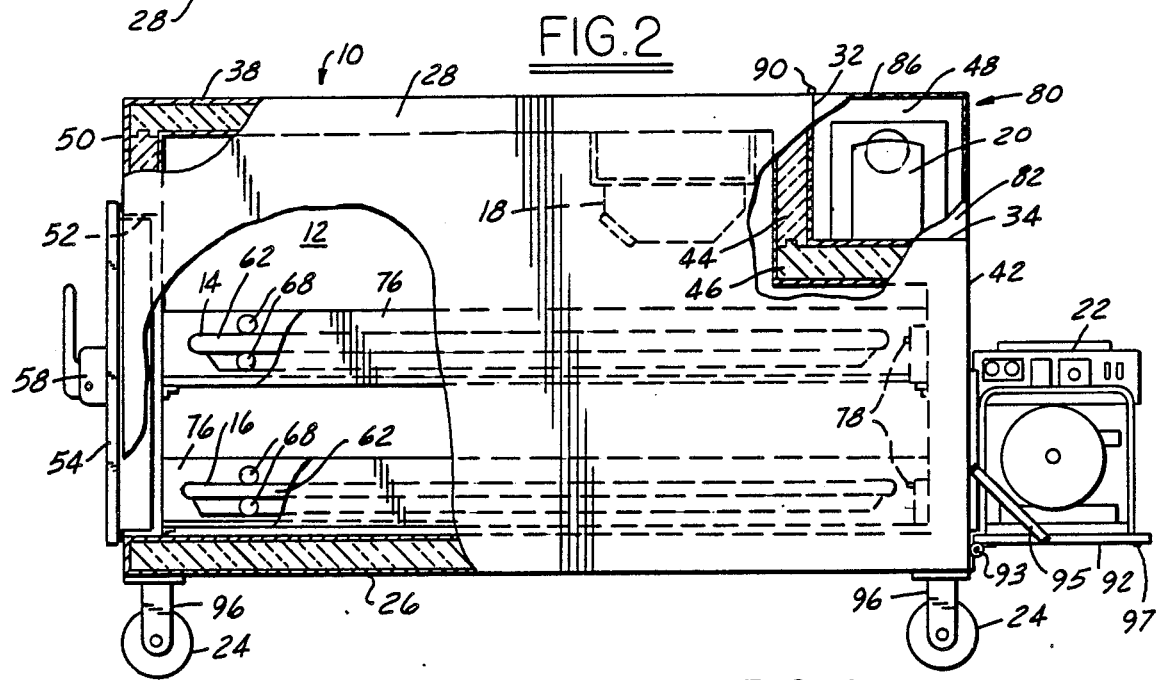
FIG. 2 is a side elevational view of the mortuary shown in FIG. 1, with parts broken away and in section.
Figure 3:
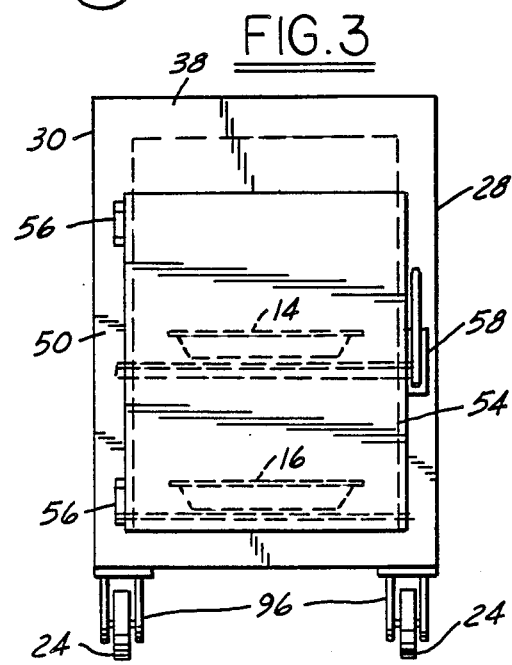
FIG. 3 is a front elevational view of the mortuary.
Figure 4:
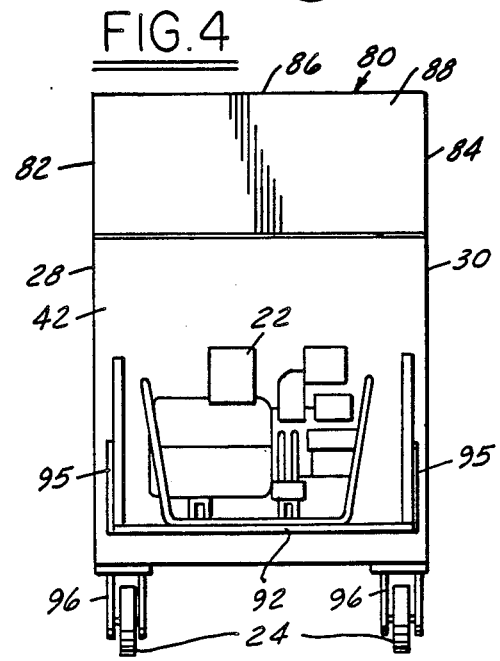
FIG. 4 is a rear elevational view.

Rollers 68 support the trays 14 and 16 for independent movement from positions entirely within the compartment 12, as in FIG. 2, through the opening 52 in the front panel of the container to the extended position of FIG. 5. Bumpers 78 serve as stops for the trays when inside the compartment.

The evaporator 18 is mounted on the top panel 38 of the container, inside compartment 12.

The compressor-condensor unit 20 for operating the evaporator 18 is mounted in the recess 48, outside the compartment 12. The compressor-condensor unit is connected to the evaporator in the usual manner to cool the coils thereof.

A cover 80, having side panels 82 and 84, a top panel 86 and a rear panel 88, is hinged at 90 to the top panel 38. When the cover is in the position closing recess 48, shown in FIGS. 1-4, side panels 82 and 84 are co-planar with side walls 28 and 30, top panel 86 is co-planar with the top panel 38, and rear panel 88 is co-planar with the rear panel 42. The cover 80 may be swung to open position about hinge 90 to service or install or remove the compressor-condensor unit.

The generator 22 is mounted on a support bracket 92 which is mounted on the rear panel 42 of the container near the bottom. The support bracket 92 is hinged at 93 for swinging movement from the horizontal support position shown in FIGS. 2 and 4 to a vertical position substantially flush with the rear panel 42 when not in use. The support bracket is held in a horizontal position by a strut 95 and can be secured in the upright or vertical position when not in use by bolts 97 which are part of the bracket assembly. The compressor-condensor unit is plugged into the generator to power the unit. Thus the mortuary unit is entirely self-contained, having its own evaporator, compressor-condensor unit and generator.

In places where electrical service is available, the generator may be dispensed with and the compressor-condensor unit may be plugged into an ordinary service outlet. The compressor-condensor unit is of a type which is capable of converting readily to the available source of electric power, either AC or DC.

In areas where electrical service is not readily available, the generator is indispensable to the operation of the mortuary. For convenience, the generator is located in close proximity to the compressor-condensor unit when mounted on the support bracket 92. It is also possible and sometimes desirable to have the generator some greater distance removed from the mortuary, as when the mortuary is indoors and it is desired to keep the exhaust gases from the generator on the outside.

The wheels 24 are mounted on brackets 96 capable of swiveling a full 360° and having means for locking the brackets in one direction and for locking the wheels against rotation.

The compressor-condensor unit is mounted on the outside of the container 10, but in the recess 48. Thus when the cover 80 is closed the clean rectangular lines of the container are retained. The recess 48 reduces somewhat the volume of the compartment, but only at the upper rear corner where there is still sufficient space to accommodate the feet of a cadaver on the upper tray.

The mortuary has only a single opening 52 at the front through which both trays 14 and 16 may be extended for loading and unloading.

I claim:

1. A self-contained, refrigerated mobile mortuary comprising an elongated container having top, bottom, side and front and rear end walls defining a single undivided interior compartment for cadavers, a single opening in said front end wall, elongated cadaver trays, means supporting said trays horizontally one above another for lengthwise movement from a position within the compartment in said container through said opening to an extended position, a single door mounted on said container for opening and closing movement relative to said opening, an evaporator mounted on said container within said compartment, a compressor-condenser unit mounted on said container outside said compartment for operating said evaporator, a generator for powering said compressor-condenser unit, and wheels supporting said mortuary for movement upon a supporting surface.

2. A mobile mortuary as defined in claim 1, including means on the rear wall of said container for mounting said generator.

3. A mobile mortuary as defined in claim 2, wherein said generator mounting means comprises a support hinged to said rear wall of said container beneath said recess for movement from a generally horizontal supporting position to a generally vertical stored position when not in use, and means on said rear wall of said container for retaining said support in said stored position.

4. A self-contained, refrigerated mobile mortuary comprising an elongated container having top, bottom, side and front and rear end walls defining an interior compartment for cadavers, an opening in said front end wall, elongated cadaver trays, means supporting said trays horizontally one above another for lengthwise movement from a position within the compartment in said container through said opening to an extended position, a door mounted on said container for opening and closing movement relative to said opening, an evaporator mounted on said container within said compartment, a compressor-condenser unit mounted on said container outside said compartment for operating said evaporator, wheels supporting said mortuary for movement upon a supporting surface, a generator for powering said compressor-condenser unit, means on said container for mounting said generator, said generator mounting means comprising a support mounted on said container for movement from a supporting position to a stored position when not in use, and means for retaining said support in its stored position.

5. A mobile mortuary as defined in claim 4, wherein said top and rear end walls of said container have portions formed to provide said container with an external recess at the top rear corner thereof, said compressor-condenser unit being mounted in said recess, and top, rear and side paneling covering said recess.

6. A self-contained, refrigerated mobile mortuary comprising an elongated container having top, bottom, side and front and rear end walls defining an interior compartment for cadavers, an opening in said front end wall, elongated cadaver trays, means supporting said trays horizontally one above another for lengthwise movement from a position within the compartment in said container through said opening to an extended position, a door mounted on said container for opening and closing movement relative to said opening, an evaporator mounted on said container within said compartment, a compressor-condenser unit mounted on said container outside said compartment for operating said evaporator, a generator for powering said compressor-condenser unit, and wheels supporting said mortuary for movement upon a supporting surface, said top and rear end walls of said container having portions formed to provide said container with an external recess at the top rear corner thereof, said compressor-condenser unit being mounted in said recess, and top, rear and side paneling covering said recess.

7. A mobile mortuary as defined in claim 6, wherein all of said walls of said container, including the portions of said top and rear end walls providing said recess, are provided with heat insulating material.

8. A self-contained, refrigerated mobile mortuary comprising an elongated container having top, bottom, side and front and rear end walls defining an interior compartment for cadavers, opening means in said front end wall, elongated cadaver trays, means supporting said trays horizontally one above another for lengthwise movement from a position within the compartment in said container through said opening means to an extended position, closure means mounted on said container for opening and closing movement relative to said opening means, an evaporator mounted on said container within said compartment, a compressor-condenser unit mounted on said container outside said compartment for operating said evaporator, a generator for powering said compressor-condenser unit, and wheels supporting said mortuary for movement upon a supporting surface, said top wall and one of said end walls of said container having portions formed to provide said container with an external recess at a top end corner thereof, said compressor-condenser unit being mounted in said recess, and top, end and side paneling covering said recess.

* * * * *